(12) United States Patent
DeSilets et al.

(10) Patent No.: US 7,135,149 B2
(45) Date of Patent: *Nov. 14, 2006

(54) POSITIONING PINS FOR MULTIWELL TEST APPARATUS

(75) Inventors: Kenneth DeSilets, Westford, MA (US); Donald Rising, Stow, MA (US)

(73) Assignee: Millipore Corporation, Billerica, MA (US)

( * ) Notice: Subject to any disclaimer, the term of this patent is extended or adjusted under 35 U.S.C. 154(b) by 484 days.

This patent is subject to a terminal disclaimer.

(21) Appl. No.: 10/167,212

(22) Filed: Jun. 11, 2002

(65) Prior Publication Data

US 2002/0192120 A1  Dec. 19, 2002

(51) Int. Cl.
*B01L 11/00* (2006.01)

(52) U.S. Cl. .................. 422/101; 422/99; 422/100; 422/102; 436/180

(58) Field of Classification Search .......... 422/99–102; 436/180
See application file for complete search history.

(56) References Cited

U.S. PATENT DOCUMENTS

| | | | | |
|---|---|---|---|---|
| 4,704,255 | A * | 11/1987 | Jolley | 422/101 |
| 5,141,718 | A | 8/1992 | Clark | |
| 5,265,754 | A | 11/1993 | Dalbo | |
| 5,462,874 | A | 10/1995 | Wolf et al. | |
| 5,650,323 | A | 7/1997 | Root | |
| 5,801,055 | A | 9/1998 | Henderson | |
| 5,837,198 | A | 11/1998 | Itani | |
| 5,972,694 | A | 10/1999 | Mathus | |
| 6,159,368 | A | 12/2000 | Moring et al. | |
| 6,309,608 | B1 * | 10/2001 | Zhou et al. | 422/131 |
| 2002/0189374 | A1 * | 12/2002 | DeSilets et al. | 73/864.51 |

FOREIGN PATENT DOCUMENTS

WO  WO 99/21958  5/1999

OTHER PUBLICATIONS

International Search Report dated Jan. 21, 2003.
"Selection of Invasive and Metastatic Subpopulations from a Heterogeneous Human Melanoma Cell Line", BioTechniques, Vo. 9, No. 3 (1990), p. 324.
1. Photograph of top plate of Multi-Screen Dual Access plate prototype, publicly provided by Millipore Corporation in Feb. 1993.
2. Photograph of three piece MultiScreen Dual Access Cell Culture System prototype, publicly provided by Millipore Corporation in Feb. 1993.

* cited by examiner

*Primary Examiner*—Yelena Gakh
*Assistant Examiner*—Jyoti Nagpaul
(74) *Attorney, Agent, or Firm*—Millipore Corporation

(57) ABSTRACT

A multiwell test apparatus comprising a multiwell filter plate and having wells that fit within the wells of a single or multiwell receiver plate is provided. The multiwell filter plate also is provided with posts which fit into holes of the receiver plate. The posts and holes are shaped to fix the position of the wells of the multiwell filter plate within the well(s) of the receiver plate and to permit controlled lateral movement of the multiwell filter plate when it is partially removed from the receiver plate so that excess liquid on the wells of the multiwell filter plate can be directed into the well(s) of the receiver plate.

14 Claims, 3 Drawing Sheets

POSITIONING PINS FOR MULTIWELL TEST APPARATUS

BACKGROUND OF THE INVENTION

This invention relates to a multiwell test apparatus suitable for promoting fluid interactions such as by monitoring cell metabolism within wells of the test apparatus. More particularly, this invention relates to such a multiwell test apparatus comprising a multiwell filter plate and a receiver plate which permits adding or removing liquid from the receiver plate without disturbing a material such as cells within the wells of the multiwell filter plate.

At the present time, multiwell test apparatus for testing samples include a multiwell filter plate, a feeding tray, a multiwell receiver plate and a lid. The wells of the multiwell filter plate are formed of a hollow, typically tubular, member with an open end to which is attached a membrane such as a microporous membrane. The tubular members can be inserted into a feeding tray containing a nutrient medium so that cells in the wells can be attached to the membrane and grown thereon. The cells are fed as nutrients pass from the nutrient medium through the membrane and to the cells at a rate controlled by the concentration gradient of nutrients from the medium to the cells. The nutrient medium in the feed tray is periodically replenished to maintain cell growth.

After the desired level of cell growth on the membranes of the wells has been attained, the multiwell filter plate can be utilized in conventional assay methods. These assay methods generally are effected by positioning the membranes and cells on the multiwell filter plate into the wells of the multiwell receiver plate, such as a 96 well receiver plate positioned below the multiwell filter plate or it just has to have the same number of wells in register with the cell/filter plate. The wells of the multiwell receiver plate contain a liquid composition to be assayed. The composition to be assayed diffuses into and then through the membrane. The resultant liquid products within the wells of the multiwell filter plate or in the wells of the multiwell receiver plate then are assayed to determine the capability of the composition being assayed to permeate the cell barrier.

An important component in the drug discovery and development process is the determination of the oral absorption and bioavailability of new compounds. In order to perform this evaluation in a cost effective, high throughput and sensitive assay, it is ideal to use an in vitro device with a multitude of wells containing cells, a small amount of assay material and automation. Classically, the determination of in vitro oral absorption characteristics is performed using a defined epithelium cell line and measuring the apparent transport rate of the drug across a monolayer of the cells. More recently it is possible to rank/order the passive transport rate of potential drug candidates using an artificial membrane barrier. The values generated from these in vitro experiments are valuable methods for screening the most likely successful drug candidates long before the oral absorption rate are validated by in vivo measurements. A typical experiment for determining the drug absorption characteristics of a known or unknown chemical compound is performed as follows. The multiwell device is seeded with epithelium cells on top of the filter in a defined nutrients medium. The same medium is also added to the single well feeding tray located below and in fluid contact with the device containing the cells. The cells are allowed to proliferate and differentiate over a number of days. The nutrient medium is periodically replaced with fresh medium to replenish exhausted nutrients and remove waste and dead cells. At the end of a growing time, the cells and multiwell device are gently washed with an isotonic buffer to remove protein and residual nutrient medium. At this time, the multiwell filter plate is transferred to the multiwell receiver plate and the chemicals to be assayed are introduced to either the compartment above the cell layer or below the cells and filter support in the multiwell receiver tray. The opposing chamber is filled with drug free buffer and the multiwell device is incubated for some period of time, typically at 37 degrees Centigrade with shaking. If multiple time points are desired, sampling from either compartment can be achieved without separating the device. The amount of drug/chemical that is transported across the cell barrier can be determined by a variety of analytical methods, but typically is determined using LC-MS/MS (Liquid Chromatography-Mass Spectrometry-Mass Spectrometry).

In prior art design, cross-talk between wells occur between the multiwell filter plate and a multiwell receiver plate due to capillary forces between the outside walls of the filter plate wells and the inside walls of the receiver plate wells. These forces result in liquid in the multiwell receiver plate moving up the wall of the well to the top of the multiwell receiver plate resulting in spill-over into an adjacent well and contamination. This contamination is unacceptable.

In addition, the multiwell filter plate and the receiver plate, be it a single well feeding tray or a multiwell receiver plate must be easily separated from each other, particularly when the multiwell test plate is processed in an automated environment.

It is also desirable to remove any droplets of liquid retained on the lower surfaces of the membranes during removal of the multiwell filter plate from the liquid in the wells of the receiver plate albeit a single well feeding tray or a multiwell receiving plate.

Accordingly, it would be desirable to provide a multiwell test apparatus comprising a receiver plate and a multiwell filter plate which facilitates removal of excess liquid from the wells of the multiwell filter plate. In addition, it would be desirable to provide such a multiwell test apparatus which prevents liquid transfer from well to well when the multiwell filter plate and the multiwell receiver plate are positioned together.

SUMMARY OF THE INVENTION

This invention will be described herein with reference to the growing and use of cells on a permeable barrier, such as a membrane, positioned and secured to the bottom of each of a multiplicity of wells. However, it is to be understood that the present invention need not be used in conjunction with cells. Other representative uses include filtration, dialysis or the like.

The present invention provides a multiwell filter plate comprising a multiplicity of wells each including a membrane for retaining a sample, such as cells on the membrane for use in a multiwell test apparatus. The multiwell filter plate is provided with at least two posts which mate with holes of a complementary receiver plate. The posts and mating holes are shaped to permit the multiwell filter plate and the receiver plate to be separated from each other easily and to permit controlled lateral transport of the multiwell filter plate relative to the receiver plate. This lateral transport permits contact of the outside well walls of the multiwell filter plate with the inside well walls of the receiver plate.

This contact provides a means for removing excess liquid from the membranes of the multiwell filter plate by surface tension and capillary action.

The posts and mating holes also are shaped and positioned so that the wells of the multiwell filter plate are spaced from and do not contact the wells of the multiwell embodiment of the receiver plate while the two plates are positioned together. This well separation prevents liquid in the wells from being transported to an adjacent well by capillary action.

VIEW OF THE DESCRIPTION OF SPECIFIC EMBODIMENTS

While the present invention is described with reference to effecting cell growth in a multiplicity of wells, it is to be understood that the present invention is applicable to manipulations involving access areas for introducing or removing a liquid to effect the desired processing, for example dialysis or diffusional separation while avoiding movement of membranes in the wells.

Figure 1:
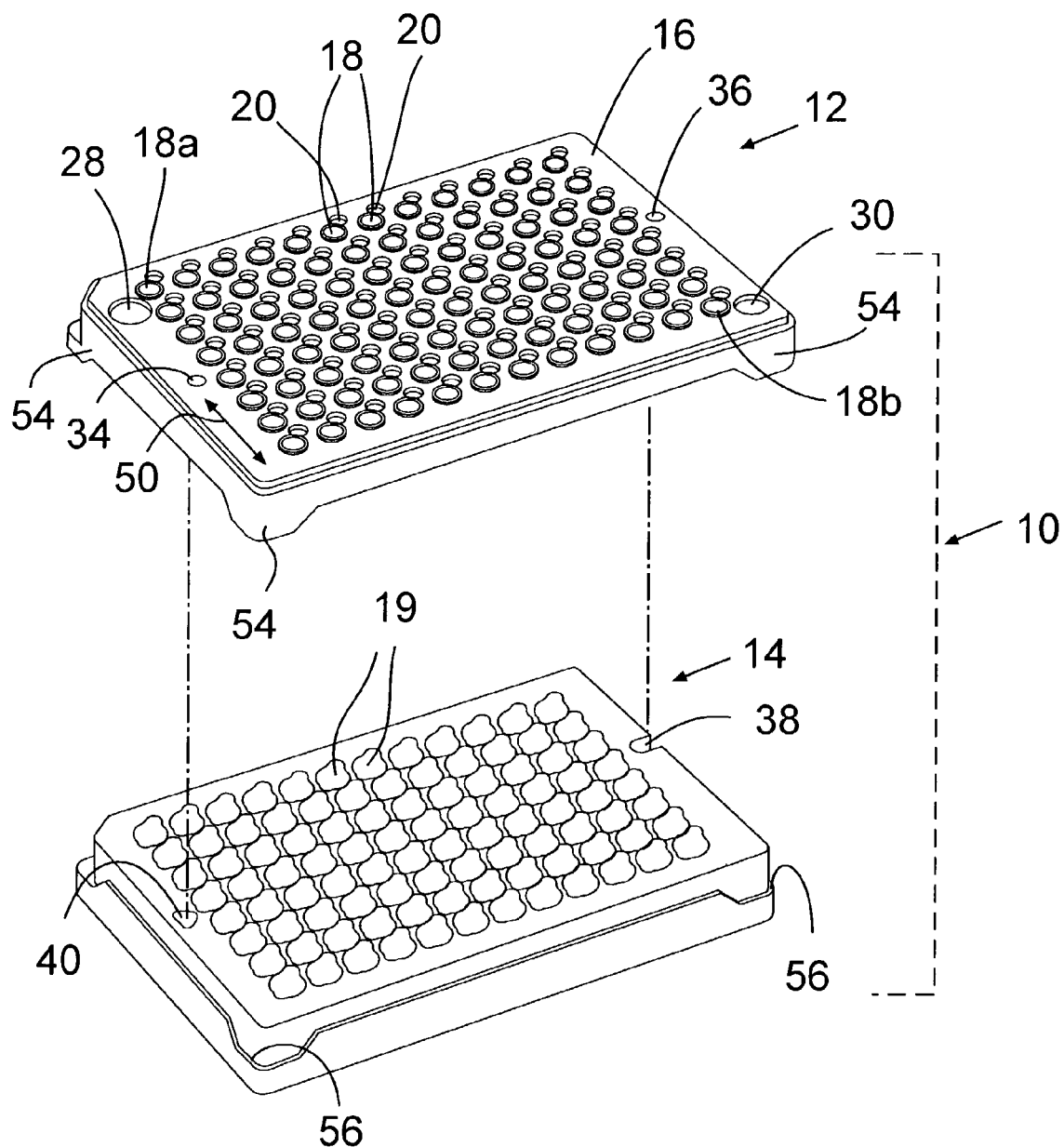
FIG. 1 is a top exploded view of a multiwell test apparatus utilizing the multiwell filter plate and multiwell receiver plate of this invention.
Figure 2:
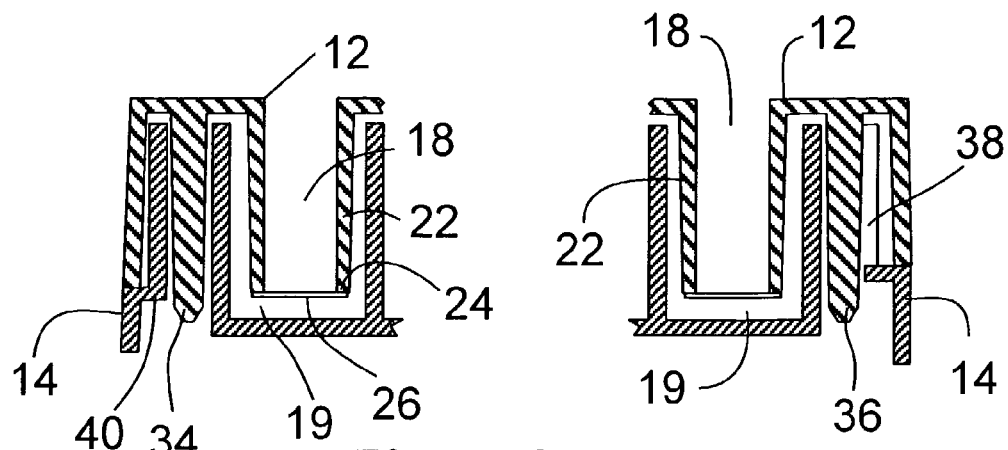
FIG. 2 is a partial cross-sectional view of a multiwell filter plate and multiwell receiver plate of this invention.

Referring to FIG. 1, a first embodiment of the multiwell test apparatus 10 of this invention comprises a multiwell filter plate 12 and a multiwell receiver plate 14. The multiwell filter plate 12 includes a plate 16 having a plurality of wells 18, each of which is paired with an access hole 20. The access holes 20 permit access through plate 16 to wells 19 of multiwell receiver plate 14 with a liquid handling device such as a syringe, cannula, pipette or the like. Each well 18 comprises a hollow, preferably tubular, member 22 and having a lower opening 24 to which is secured a permeable barrier 26 such as a microporous membrane. (FIG. 2). By permeable barrier, it is meant that the barrier is permeable to liquids and gases but not particulate materials over the rated pore size of the barrier. Membranes, especially microporous membranes are a preferred material for the barrier, although other materials such as ultrafiltration membranes, glass mats or fabrics, or woven or non-woven plastic materials may be used. The member 22 is hollow and may be formed in a variety of shapes. Tubular designs are preferred and the industry standard for such wells, although wells of other shapes such as triangular, rectangular, square or hexagonal may be used.

Access holes 28 and 30 provide access to a feeding tray (not shown) into which liquid or gel nutrient medium is introduced and removed prior to utilizing the multiwell filter plate 12 with the multiwell receiver plate 14. Nutrient medium can be removed and introduced through access holes 28 and 30 with a conventional liquid handling device, such as a syringe, extending through access holes 28 and 30.

Figure 2A:
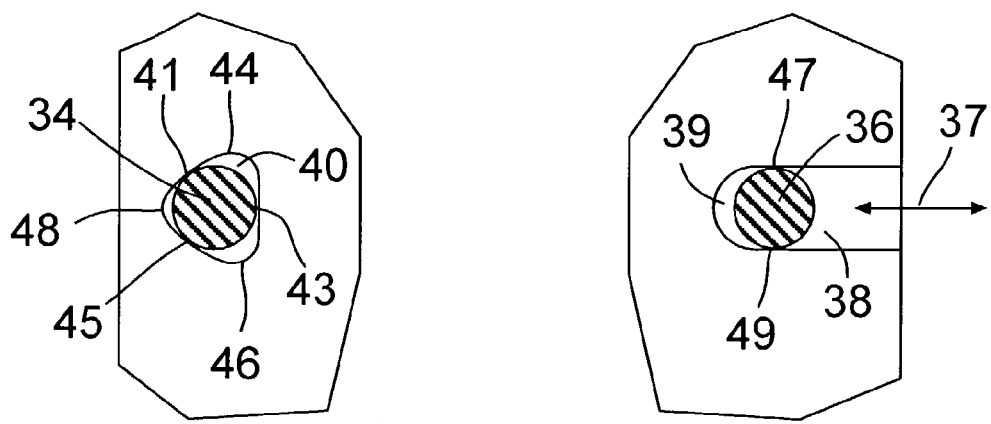
FIG. 2A is a partial sectional top view of posts and mating holes for receiving the multiwell filter plate to the multiwell receiver plate of this invention.

Multiwell filter plate 12 is provided with posts 34 and 36 which fit respectively in holes 40 and 38 of multiwell receiver plate 14 when multiwell receiver plate 14 is positioned below multiwell filter plate 12. Referring to FIG. 2A, hole 40 has a triangular-like cross-section, preferably with rounded interstices 44, 46 and 48. Hole 38 comprises a slot which permits post 36 to move laterally in the direction of arrow 37. Posts 34 and 36 are positioned different from each other relative to a center-line of the plate in the direction of arrow 50 (or asymmetrically opposed to each other) so that well 18a is always in the upper left hand position while well 18b is always in the lower right hand position shown in FIG. 1. By so positioning wells 18a and 18b, all the wells 18 in multiwell filter plate 12 can be identified by their position.

The use of multiwell test apparatus 10 is exemplified with reference to FIG. 1. As shown in FIG. 1, the multiwell filter plate 12 is positioned above multiwell receiver plate 14. The multiwell receiver plate 14 is positioned such that each of the membranes 26 (FIG. 2) of each of the wells 18 extends into only one well 19 of the multiwell receiver plate 14. Each of the wells 18 has associated therewith an access hole 20 which permits access to a portion of well 19 of the multiwell receiver plate 14 utilized during a sample assay step. The multiwell filter plate 12 can be provided with four legs 54 which fit into recesses 56 of multiwell receiver plate 14 thereby to provide mechanical stability of multiwell filter plate 12. The legs 54 also serve to position the membranes 26 to avoid contact with the bottom surfaces of the wells 19 thereby to promote contact of liquid with the membranes 26.

Figure 3:
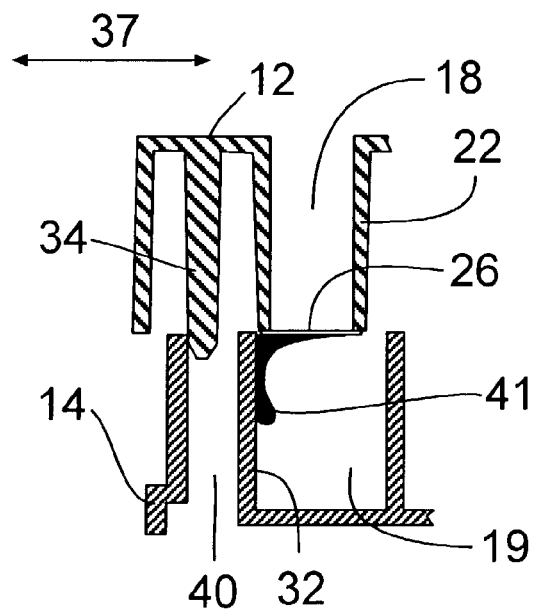
FIG. 3 is a cross-sectional view of the position of the multiwell filter plate and multiwell receiver plate when removing excess liquid from a membrane of a multiwell filter plate.

Referring to FIGS. 2 and 2A, the posts 34 and 36 fit respectively into hole 40 and slot 38. Hole 40 is shaped with a three-sided perimeter so that post 34 contacts the walls of the hole 40 at three points 41, 43 and 45. This mode of contact prevents multiwell filter plate 12 from moving laterally with respect to the multiwell receiver plate 14. Post 36 contacts the walls of slot 38 at two points 47 and 49 so that part to part variations, or misalignment can only be accommodated in the direction shown by arrow 37. The lowermost ends of posts 34 and 36 are beveled to promote ease of insertion of the posts 34 and 36 into holes 40 and 38. In addition, as shown in FIG. 3, since the tip of post 34 is smaller than hole 40, and post 34 is longer than well 22 and since the tip of post 36 is smaller than hole 38 and post 36 is longer than well 22, this permits the multiwell filter plate 12 to move laterally as exemplified by arrow 37 when it is partially lifted from the multiwell receiver plate as shown in FIG. 3. This lateral movement is not limited to the direction or arrow 37 if the posts 34 and 36 taper uniformly as shown. This lateral movement permits contact of droplet 41 onto inner wall 32 of well 19 so that droplet 41 moves into well 19 from the membrane 26. This touch off of the droplet 41 prevents cross-talk contamination of the liquid into an adjacent well to the well 19 shown.

It is to be understood that the posts 34 and 36 can be the same length or shorter than the wells 18 so long as they are longer than holes 40 and 38. Controlled lateral movement of the multiwell filter plate 12 is effected by shaping the posts 34 and 36 and the holes 40 and 38 so that when the posts 34 and 36 are partially removed from holes 40 and 38 a space is formed between the posts 34 and 36 and the interior walls of holes 40 and 38 which permits lateral movement of the posts 34 and 36 within the holes 40 and 38 and, thus the lateral movement of the multiwell filter plate so that touch off of the droplets 41 is effected. This can be effected, for example, by forming inclined surfaces on the posts 34 and 36 from the top of the posts to the bottom of the posts where the walls of the holes 40 and 38 are vertical.

Figure 4:
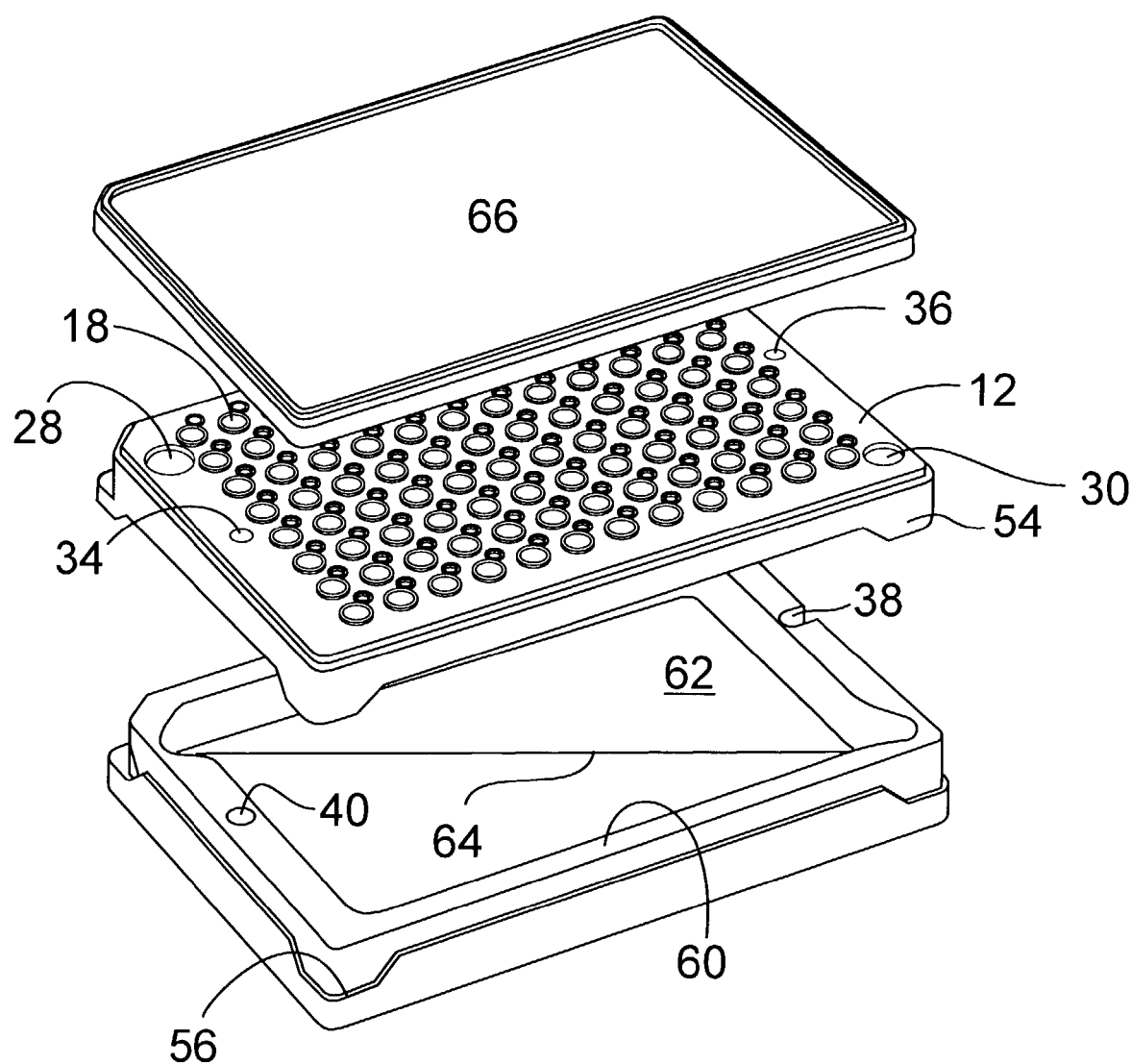
FIG. 4 is a view of an additional embodiment of a multiwell filter plate and single receiver plate.

FIG. 4 shows the same multiwell filter plate 12 in use with a single well plate 60. In this embodiment, the single well receiving plate 60 contains all of the elements of the multiwell receiving plate 14 of FIG. 1 except for the number of individual wells. It is used mainly for feeding of the cells that may be grown in the filter plate. It may also be used in those applications where the filtrate from the wells of the filter plate are not collected fro analysis and merely directed to the drain. The posts 34, 36 have the same configuration and dimensions as described above in relation to the multiwell receiving plate 14 of FIG. 1. Likewise, the holes 38,40 of the single well plate 60 are identical to those of the embodiment described above in relation to the multiwell receiving plate 14 and perform the exact same function. Additionally, the single well plate 60 may have the recesses 56 of multiwell receiver plate 14 into which the four legs 54 of the multiwell filter plate 12 fit to provide mechanical stability of multiwell filter plate 12. The legs 54/recesses 56 also serve to position the membranes (not shown) of the multiwell filter plate 12 to avoid contact with the bottom surface of the wells 18 of the filter plate 12 with the bottom surface of the single well 62 of the plate 60 thereby to promote contact of liquid with each well 18 of the filter plate 12. The single well plate 60 may have a flat bottom (not shown) or it may have an inclined bottom 64 that allows for the flow of liquid from one end of the plate 60 adjacent the access hole 28 of the multiwell filter plate 12 to the other end of the single well plate 60 adjacent access hole 30 of the multiwell filter plate 12. In this way, one can easily change or add fluid to the single well plate 60 through the one or more access holes 28,30 of the filter plate 12 without disturbing the cells on the membrane of the filter plate 12. Also shown in FIG. 4 is the optional cover 66 which is placed over the top of the filter plate 12 to prevent contamination and/or evaporation of liquid from the test system.

What we claim:

1. A multiwell test apparatus comprising a multiwell filter plate and a receiver plate supporting said multiwell filter plate,
   said multiwell filter plate having a multiplicity of first wells extending from a plate, each of said wells comprising (a) a hollow member having two openings and extending from said plate and (b) a permeable barrier secured about said lower opening, and two posts formed on the undersurface of the filter plate which fit into holes on the upper surface of said receiver plate,
   said receiver plate having one or more wells to accommodate said first wells of the filter plate,
   said posts and said holes being shaped to prevent contact of said first wells and said second one or more wells when said posts are fully positioned within said holes and to permit controlled lateral movements of said multiwell filter plate to permit contact of said first wells and said second one or more wells when said posts are partially removed from said holes.

2. The multiwell test apparatus of claim 1 wherein said posts have a beveled surface at least along the lowermost portions.

3. The multiwell test apparatus of claim 1 wherein one of said holes has a three-sided perimeter and a second of said holes is shaped as a slot, an oval, or rectangle.

4. The multiwell test apparatus of claim 1 wherein one of said holes has a three-sided perimeter and a second of said holes is shaped as a slot.

5. The multiwell apparatus of claim 1 having more than two posts and two holes.

6. The multiwell test apparatus of claim 1 wherein an access hole through said filter plate is positioned adjacent each of said first wells to permit access to the one or more wells of the receiver plate.

7. The multiwell test apparatus of claim 1 wherein the permeable barrier is selected from the group consisting of a membrane, a glass mat, a glass fabric, a woven plastic sheet and a non-woven plastic sheet.

8. The multiwell test apparatus of claim 1 wherein the receiving plate is a multiwell receiving plate.

9. The multiwell test apparatus of claim 1 wherein the number of second one or more wells of the receiving plate correspond in number and position to the number of first wells of the filter plate.

10. The multiwell test apparatus of claim 1 wherein the number of one or more wells of the receiving plate correspond in number and position to the number of first wells of the filter plate and wherein said second one or more wells each are sized to accommodate one of said first wells.

11. A multiwell test apparatus comprising a multiwell filter plate and a receiver plate supporting said multiwell filter plate,
    said multiwell filter plate having a multiplicity of first wells extending from a plate, each of said wells comprising (a) a hollow member having two openings and extending from said plate and (b) a permeable barrier secured about said lower opening, and two posts formed on the undersurface of the filter plate which fit into holes on the upper surface of said receiver plate,
    said receiver plate having one or more wells to accommodate said first wells of the filter plate,
    said posts and said holes being shaped to prevent contact of said first wells and said second one or more wells when said posts are fully positioned within said holes and to permit controlled lateral movements of said multiwell filter plate to permit contact of said first wells and said second one or more wells when said posts are partially removed from said holes and wherein one of said holes has a three-sided perimeter and a second of said holes is shaped as a slot, an oval or rectangle.

12. The apparatus of claim 11 wherein the second of said holes is shaped as an oval.

13. The apparatus of claim 11 wherein the second of said holes is shaped as a rectangle.

14. A multiwell test apparatus comprising a multiwell filter plate and a receiver plate supporting said multiwell filter plate,
    said multiwell filter plate having a multiplicity of first wells extending from a plate, each of said wells comprising (a) a hollow member having two openings and extending from said plate and (b) a permeable barrier secured about said lower opening, and two posts formed on the undersurface of the filter plate which fit into holes on the upper surface of said receiver plate,
    said receiver plate having one or more wells to accommodate said first wells of the filter plate,
    said posts and said holes being shaped to prevent contact of said first wells and said second one or more wells when said posts are fully positioned within said holes and to permit controlled lateral movements of said multiwell filter plate to permit contact of said first wells and said second one or more wells when said posts are partially removed from said holes and wherein one of said holes has a three-sided perimeter and a second of said holes is shaped as a slot.

* * * * *